US005628766A

United States Patent [19]
Johnson

[11] Patent Number: 5,628,766
[45] Date of Patent: May 13, 1997

[54] METHOD OF USING A MINI-SCREW TO ANCHOR A SUTURE

[76] Inventor: Lanny L. Johnson, 4528 Hagadorn, East Lansing, Mich. 48823

[21] Appl. No.: 496,407

[22] Filed: Jun. 29, 1995

[51] Int. Cl.$^6$ ................................................ A61B 17/00
[52] U.S. Cl. ............................................ 606/232; 606/73
[58] Field of Search ..................... 606/232, 104, 606/73, 75, 187, 60, 65, 66, 72, 76; 623/13, 11; 411/103, 136, 137, 142, 172, 173, 218, 395, 422

[56] References Cited

U.S. PATENT DOCUMENTS

| 3,842,824 | 10/1974 | Neufeld | 606/73 |
| 5,108,399 | 4/1992 | Eitenmuller et al. | 606/76 |
| 5,116,337 | 5/1992 | Johnson | 606/73 |
| 5,129,904 | 7/1992 | Illi | 606/72 |
| 5,236,431 | 8/1993 | Gogolewski et al. | 606/72 |

FOREIGN PATENT DOCUMENTS

| 2747312 | 4/1979 | Germany | 606/73 |
| WO94/28811 | 12/1994 | WIPO | 606/73 |

*Primary Examiner*—Jeffrey A. Schmidt
*Attorney, Agent, or Firm*—Cushman Darby & Cushman IP Group of Pillsbury Madison & Sutro LLP

[57] ABSTRACT

A surgical device is provided for anchoring suture into bone. The device includes a threaded portion having rounded exterior thread edges. An aperture for carrying suture passes through the threaded portion at a location intermediate the ends of the threaded position, the aperture extending in a direction substantially transversely to the longitudinal axis of the device. When the device is inserted within a cavity in the bone having a threaded sidewall, the suture is compressed between the threads of the device and the sidewall.

1 Claim, 1 Drawing Sheet

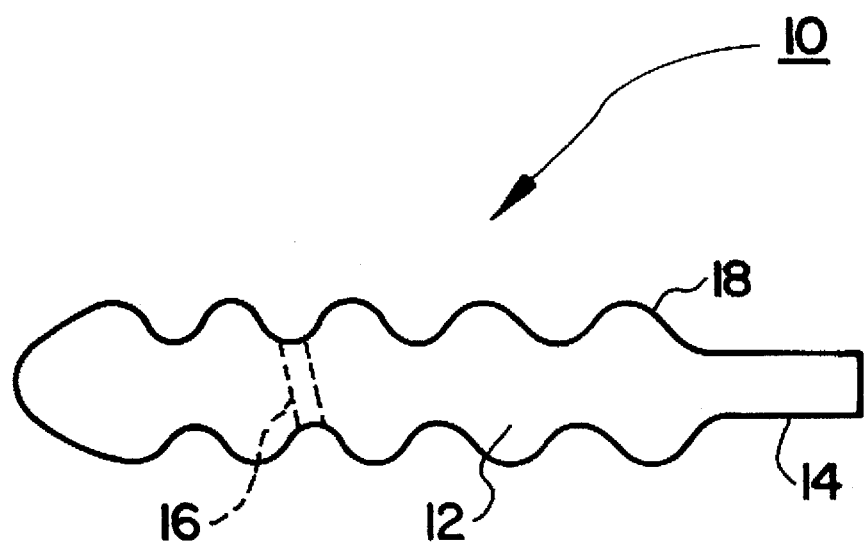

METHOD OF USING A MINI-SCREW TO ANCHOR A SUTURE

BACKGROUND OF THE INVENTION

1. Field of the Invention

The present invention relates to a surgical device of the type which screws into bone in order to anchor suture to the bone for orthopaedic surgical procedures.

2. Prior Art

The use of screws as suture anchors is well known. For example, one such device is described in U.S. Pat. No. 4,632,100 by Somers et al. wherein a surgical screw is provided with a longitudinal bore within which suture is secured so that when the screw is implanted in bone, the ends of the suture extend from the proximal end of the screw so as to be accessible to the surgeon.

Other known screw anchors have projecting tips located at the proximal ends of the screws, the tips including a transverse aperture through which suture may be threaded by the surgeon.

A still further surgical screw is disclosed in U.S. Pat. No. 5,116,337 by Johnson which includes a radially extending hole located adjacent to the end of the screw. However, the purpose of the hole is not to receive suture, but accept a wire which prevents the screw from turning when a driver used to force the screw into place within the bone is detached from the screw.

SUMMARY OF THE INVENTION

The present invention is directed to a suture anchor which is provided with a threaded portion having rounded thread ends and an aperture which is oriented transversely to the longitudinal axis of the anchor and passes through the anchor intermediate the ends of the threaded portion of the screw. When suture is passed through the aperture and the threaded portion is implanted in the bone, suture ends extending from the aperture are compressed between the screw threads and the surrounding bone to firmly anchor the suture. In the case where the anchor is formed of a biodegradable material, the initial mechanical attachment of the suture transforms to a biological adherence as the screw degrades.

BRIEF DESCRIPTION OF THE DRAWINGS

The invention will be described in further detail with respect to the accompanying drawing which illustrates a preferred embodiment of the invention.

DETAILED DESCRIPTION OF THE INVENTION

Referring to the drawing, a surgical screw anchor is shown which is generally designated as 10. The anchor preferably is formed from a conventional biodegradable material suitable for surgical applications. According to a preferred embodiment of the invention, anchor 10 includes a threaded portion 12 and a portion 14 formed at the proximal end of the anchor adapted to be engaged by a conventional driver by which the threaded portion is moved into operative position within the bone. Preferably, portion 14 is dimensioned at its juncture with threaded portion 12 to provide a weakened point such that when the screw is firmly positioned within the bone, further actuation by the driver causes portion 14 to shear from its connection with threaded portion 12 thereby leaving no material projecting from the proximal end of the implanted portion 12.

Intermediate the ends of the threaded portion 12, an aperture 16 is provided which extends through the screw in a direction substantially transversely to the screw's longitudinal axis. The aperture is dimensioned to receive a length of suture material.

The threads themselves are formed with rounded outer edges 18, rather than sharp edges customarily found on screw threads. The purpose for this now will be explained.

In the preparation of the site for the implantation, a series of increasingly larger instruments are inserted into a cavity formed in the bone. This technique is generally described in the previously identified U.S. Pat. No. 5,116,337. As a result, the wall of the cavity is compacted bone having improved mechanical properties which aid in solid attachment of the screw within the cavity. Additionally, the compaction permits a biological response to be initiated between the compacted bone and the materials which interface with the cavity's wall. The wall of the cavity is then tapped so as to provide female threads for receiving the surgical screw. The exterior diameter of the tap is dimensioned to be greater than the exterior diameter of the anchor's threads.

When the surgeon completes the preparation of the site, as just described, a length of suture is passed through aperture 16 of the anchor, and the threaded portion 12 is driven into the cavity by conventional means. Because of the differences in diameters between the cavity's female threads and those of portion 12, and inasmuch as the threaded edges 18 are rounded, the ends of suture extending from aperture 16 are not severed as the anchor is implanted within the cavity. Instead, the suture is compressed between the threads of portion 12 and the threaded wall of the cavity. As a result, the suture is firmly anchored for the surgeon's use.

As stated previously, once the anchor 10 is firmly implanted, portion 14 shears off. Alternatively, if shearing fails or this feature is not provided for in the screw's design, the proximal portion 14 can be severed from the remainder of the anchor by conventional means provided that care is exercised to not cut the suture in the process.

While a preferred embodiment of the invention has been disclosed, variations are contemplated coming within the scope of the accompanying claims.

What is claimed is:

1. A process for anchoring suture into bone, comprising:

forming a cavity within the bone having a compacted sidewall;

threading the sidewall of the cavity; and inserting a threaded portion of a suture anchor within the cavity, said portion including threads with rounded exterior edges and having an exterior diameter less than that of the threaded sidewall, said anchor further including an aperture passing through the anchor in a substantially transverse direction to a longitudinal axis of the anchor and at a location intermediate the ends of the threaded portion, said aperture receiving a length of suture having ends projecting from the aperture which are compressed between the threads of the anchor and the sidewall when said anchor is inserted within the cavity.

* * * * *